(12) United States Patent
Frigstad et al.

(10) Patent No.: US 8,764,660 B2
(45) Date of Patent: Jul. 1, 2014

(54) METHODS AND APPARATUS FOR COMBINED AUDIBLE AND ULTRASOUND INSPECTION OF OBJECTS, INCLUDING PATIENTS

(75) Inventors: Sigmund Frigstad, Sør Trøndelag (NO); Jean-Francois Gelly, Mougins (FR); Hans Garmann Torp, Midtnorge (NO)

(73) Assignee: General Electric Company, Schenectady, NY (US)

( * ) Notice: Subject to any disclaimer, the term of this patent is extended or adjusted under 35 U.S.C. 154(b) by 1203 days.

(21) Appl. No.: 11/872,884

(22) Filed: Oct. 16, 2007

(65) Prior Publication Data
US 2009/0099446 A1   Apr. 16, 2009

(51) Int. Cl.
*A61B 8/00* (2006.01)
(52) U.S. Cl.
USPC ............ 600/443; 600/407; 600/437; 600/459
(58) Field of Classification Search
USPC .......................................... 600/437, 443, 459
See application file for complete search history.

(56) References Cited

U.S. PATENT DOCUMENTS

| | | | | |
|---|---|---|---|---|
| 6,106,472 | A * | 8/2000 | Chiang et al. | 600/447 |
| 6,471,649 | B1 * | 10/2002 | Saccardo et al. | 600/437 |
| 7,303,530 | B2 | 12/2007 | Barnes et al. | |
| 7,393,326 | B2 * | 7/2008 | Bindefeld | 600/453 |
| 2004/0225476 | A1 | 11/2004 | Tien | |
| 2008/0281206 | A1 * | 11/2008 | Bartlett et al. | 600/459 |
| 2009/0312638 | A1 * | 12/2009 | Bartlett | 600/443 |

FOREIGN PATENT DOCUMENTS

| | | |
|---|---|---|
| JP | 56-071212 U1 | 6/1981 |
| JP | 56-133809 U1 | 10/1981 |
| JP | 57-123110 U1 | 7/1982 |
| JP | 2001-333899 A | 12/2001 |
| JP | 2004-329909 A | 11/2004 |
| WO | WO 2005/037096 A1 | 4/2005 |

OTHER PUBLICATIONS

Duvall et al., Can Hand-Carried Ultrasound Devices be Extended for Use by the Noncardiology Medical Community?, Echocardiography: A Jnrl. of CV Ultrasound & Allied Tech, vol. 20, No. 5, 2003, pp. 471-476.

Tianrong Xie et al., Rapid Screening of Cardiac Patients with a Miniaturized Hand-Held Ultrasound Imager—Comparisons with Physical Examination and Conventional Two-Dimensional Echocardiography, Clin. Cardiol. vol. 27, 241-245 (Apr. 2004).

* cited by examiner

*Primary Examiner* — James Kish
*Assistant Examiner* — Joel Lamprecht
(74) *Attorney, Agent, or Firm* — The Small Patent Law Group; Dean D. Small (57) ABSTRACT

An acquisition component is provided that includes an audible sound sensor configured to receive audible sounds within a sensing area and a multi-element ultrasound transducer configured to emit ultrasound signals and to receive reflections of the ultrasound signals in the same sensing area. The audible sound sensor and the multi-element ultrasound transducer may be configured to be simultaneously operable.

21 Claims, 5 Drawing Sheets

METHODS AND APPARATUS FOR COMBINED AUDIBLE AND ULTRASOUND INSPECTION OF OBJECTS, INCLUDING PATIENTS

BACKGROUND OF THE INVENTION

This invention relates generally to audible and ultrasound inspection of objects, including living patients.

Auscultation is a common method used by general practitioners to diagnose heart or lung disease. Auscultation requires a conventional, electronic or digital stethoscope. A conventional acoustic stethoscope uses an air cavity (e.g., a Helmholtz resonator) coupled to a duct, which itself is inserted into an ear. Known electronic stethoscopes passively pick up ultrasound signals using a microphone and then use electronic amplifiers and filters to electronically enhance the signals. Digital stethoscopes are electronic stethoscopes with the capability of storing the sound digitally and transferring the sound to a computer for analysis.

More recently, ultrasound echoes have been used by specialists to confirm or reject some findings from auscultation. It has been shown that simultaneous auscultation and echo adds value to certain diagnostic examinations.

Portable ultrasound machines are known and are used in much the same way as larger ultrasound scanners. However, ultrasound imaging devices that fit in the palm of one's hand are currently under development. These palm-top devices have the potential to become visual "stethoscopes" that can complement auscultation during a physical exam. (See, for example, Xie T, Chamoun A J, McCulloch M, Tsiouris N, Birnbaum Y, Ahmad M., "Rapid screening of cardiac patients with a miniaturized hand-held ultrasound imager—comparisons with physical examination and conventional two-dimensional echocardiography," Clin Cardiol. 2004 Apr.;27/4:241-5, Duvall W L, Croft L B, Goldman M E, "Can hand-carried ultrasound devices be extended for use by the noncardiology medical community?" Echocardiography. 2003 Jul.;20/5: 471-6, and Kotler M N, Segal B L, Parry W R, "Echocardiographic and phonocardiographic correlation of heart sounds and murmurs," Cardiovasc Clin. 1978;9/2:39-57.) However, with presently known palm-top devices, it still requires at least two persons or at least an exceptionally experienced user to perform echo and auscultation examinations simultaneously.

Performing auscultation and echo simultaneously requires two separate devices, either in form of a stethoscope and an echo machine or two separate probes connected to one ultrasound scanner (e.g., separate ultrasound and phono probes).

Moreover, while visual ultrasound stethoscopes may be superior to ordinary stethoscopes in detecting cardiac disease or in other diagnostic applications, a visual ultrasound stethoscope cannot completely replace an ordinary stethoscope because ultrasound signals do not penetrate air-filled organs like the lung and intestines. Thus, for example, when a physician is doing ward rounds with a hand-held scanner, he still needs to carry an acoustic stethoscope.

BRIEF DESCRIPTION OF THE INVENTION

In accordance with an embodiment, an acquisition component is provided that includes an audible sound sensor configured to receive audible sounds within a sensing area and a multi-element ultrasound transducer configured to emit ultrasound signals and to receive reflections of the ultrasound signals in the same sensing area.

In accordance with another embodiment, an inspection apparatus is provided that includes an acquisition component as described above, plus an ultrasound imaging apparatus that includes an ultrasound transmitter, an ultrasound receiver, a processor and a display. The ultrasound imaging apparatus is configured to display an image in accordance with the received, reflected ultrasound signals. The inspection apparatus further includes an audible sound receiver configured to produce audible sounds in accordance with the received audible sounds.

In accordance with yet another embodiment, a method for performing auscultation using an inspection apparatus as described above is provided. The method includes performing an auscultation of a patient's organ using the acquisition component at a sensing area of the patient while simultaneously performing an ultrasound echo at the same sensing area of the patient.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Embodiments of the present invention integrate a sound and ultrasound sensor into one device, making it unnecessary for a physician to carry a separate stethoscope, for example, while making rounds. In addition, embodiments of the present invention are able to perform auscultation and echo simultaneously, without requiring a physician to be exceptionally experienced or having to obtain the services of an assistant. Embodiments of the present invention have the capability of recording ultrasound images and of enabling a physician to listen to and/or visualize sounds from the body, all from a single sensing area, either separately or simultaneously.

Figure 1:
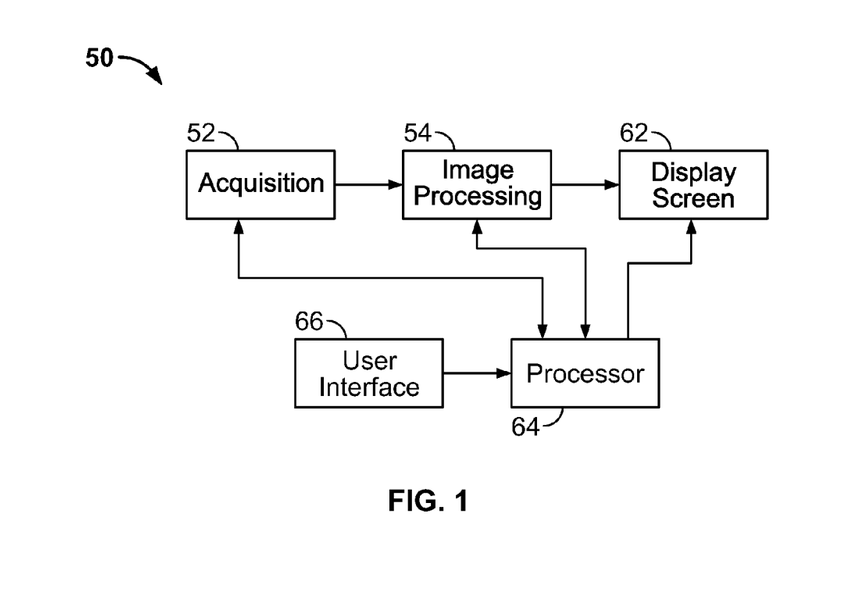
FIG. 1 is a block diagram of an inspection apparatus constructed in accordance with an embodiment of the present invention.

Various embodiments of the invention provide an inspection apparatus 50 as shown in FIG. 1. The inspection apparatus 50 may be any type of system, for example, different types of inspection apparatus, such as an ultrasound imaging system, an x-ray imaging system, a computed-tomography (CT) imaging system, a single photon emission computed tomography (SPECT) system, a positron emission tomography (PET) imaging system, a nuclear medicine imaging system, a magnetic resonance imaging (MRI) system, and combinations thereof (e.g., a multi-modality imaging system), among others. However, the various embodiment are not limited to medical imaging systems or imaging systems for imaging human subjects, but may include non-medical inspection apparatus for imaging non-human objects and for performing non-destructive imaging or testing, security imaging (e.g., airport security screening), etc.

The inspection apparatus 50 generally includes an acquisition component 52 configured to acquire image data (e.g., ultrasound image data), and, in some embodiments of the present invention, audible sounds. The acquisition component 52 may be, for example, a probe, scanner or other similar device for scanning an object or volume of interest. The acquisition component 52 is connected to an image processing component 54. The image processing component 54 is any type of image processor capable of processing the acquired image data and configuring and/or formatting the processed image data for display on a display screen 62 as described in more detail herein. The display screen 62 may be any type of screen capable of displaying images, graphics, text, etc. For most hand-carried or pocket-sized inspection apparatus 50 embodiments, a liquid crystal display (LCD) is provided as display screen 62, but in some embodiments, display screen 62 may be a cathode ray tube (CRT) or a plasma screen, or another type of display.

A processor 64 (e.g., computer) or other processing unit controls the various operations within the inspection apparatus 50. For example, the processor 64 may receive user inputs from a user interface 66 and display requested image data or adjust the settings for the displayed image data. In some cases the image processor 54 and processor 64 will be located in the same processing device.

Figure 2:
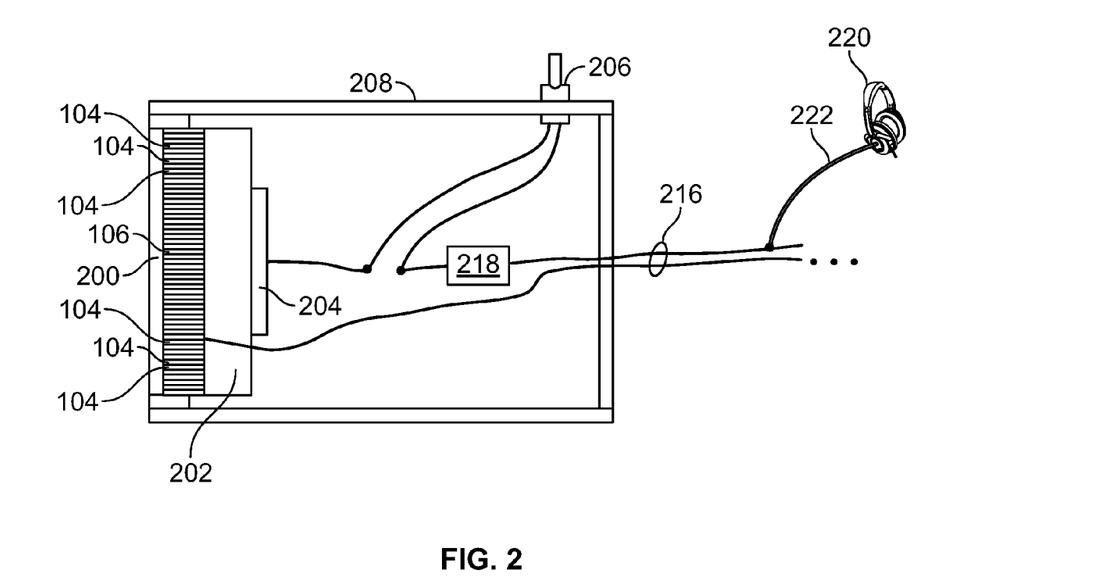
FIG. 2 is an axial cross-sectional drawing of an acquisition component configured as a probe having an audible sound sensor configured to receive audible sounds within a sensing area and a multi-element ultrasound transducer configured to emit ultrasound signals and to receive reflections of the ultrasound signals in the same sensing area.

FIG. 2 is an axial cross-sectional drawing of an acquisition component 52 configured as a probe having an audible sound sensor 204 configured to receive audible sounds within a sensing area and a multi-element ultrasound transducer 106 configured to emit ultrasound signals and to receive reflections of the ultrasound signals in the same sensing area. The audible sound sensor 204 and the multi-element ultrasound transducer 106 are configured to be simultaneously operable or separately operable, or both.

More particularly, in some embodiments, acquisition component 52 comprises a multi-element ultrasound transducer 106 comprising an array of ultrasound transducer elements 104 and having a lens 200 (for example, a silicon rubber RTV lens) mounted at the front of a housing 208. Lens 200 is acoustically coupled to the array of ultrasound transducer elements 104. The multi-element ultrasound transducer further includes a backing 202 on or behind which one or more audible sound sensors 204 are mounted. The audible sound sensor can be any device capable of generating an electrical signal representative of an audible sound, wherein the electrical signal is capable of being detected and transformed back into the audible sound or a useful approximation thereof. Examples of such audible sound sensors 204 include, but are not limited to, accelerometers, microphones, capacitive microphones, hydrophones, and even geophones.

Examples of ultrasound sensor embodiments include sensors having a stack of piezoelectric material (ceramic or single crystal) and matching layers on front, with a backing layer on the bottom. The backing layer can be thick (e.g., a few mm of absorbing material) or very thin or not present (e.g., dematching layer technology). For example, a velocity or acceleration sensor can be attached directly on the rear side of the backing or directly on the stack with no backing. Another example of an ultrasound sensor is a capacitive micromachined (cMUT) device that comprises a thin membrane that can be designed to have a resonance in flexion at audio frequency range, amplifying the received audio signal on the velocity or acceleration sensor attached or integrated in. cMUT technology is particularly well suited for integration of sensor and amplifier with the ultrasound array. This type of sensor can also be coupled to an air cavity of a Helmhotz resonator or any other mechanical resonant structure, with amplified pressure being detected by a microphone.

Examples of sound sensor embodiments include solid/liquid (high acoustic impedance) sensors and air (low impedance) coupled sensors. Solid/liquid sensors use acceleration or velocity sensors (e.g., accelerometer, hydrophone, or geophone, or a combination of these) while air coupled sensors may use microphones.

Various technologies can be use for the sensors, including, but not limited to, thickness mode or flexural mode resonator technologies, piezoelectric or electrodynamic technologies, capacitive (e.g., condenser, electret) technologies, and/or electrostrictive, electro-acoustic coupling, or optical detector technologies.

In some embodiments, a switch 206 is provided that is configured to selectively enable or disable audible sound sensor 204 and/or multi-element transducer 106. For example, in one embodiment, a small locking push-button switch 206 is provided on housing 208 that short circuits audible sound sensor 204 when pressed to provide zero voltage across a cable that carries an electrical signal from audible sound sensor 204 when switch 206 is in its open position. A variety of different switching arrangements can be used for audible sound sensor 204 and/or multi-element transducer 106, including arrangements in which the switching is provided other than on or in housing 208. The selection of a suitable switching arrangement can be a design choice for an electrical or electronics design engineer.

In some embodiments, an internal audio amplifier 218 is provided inside housing 208. Power for amplifier 218 may be provided via electrical cable 216 and/or by an internal rechargeable or replaceable battery within housing 208. An earphone or headphone 220 is operably coupled to audible sound sensor 204 via amplifier 218. In embodiments in which an internal audio amplifier 218 is provided, a separate earphone cable 222 to earphone 220 may exit housing 208, or earphone cable 222 may branch off from electrical cable 216. The audible signal applied to earphone 220 may also be routed through a separate component via electrical cable 216 and from the separate component to earphone 220. In some other embodiments, audio amplifier 218 is contained within another system component and earphone 220 may simply be plugged into the component in which the amplifier is housed. Earphone 220 may be replaced with loudspeakers, and in other embodiments, a wireless transceiver (e.g. Bluetooth) may be used to connect to wireless headphones.

Figure 3:
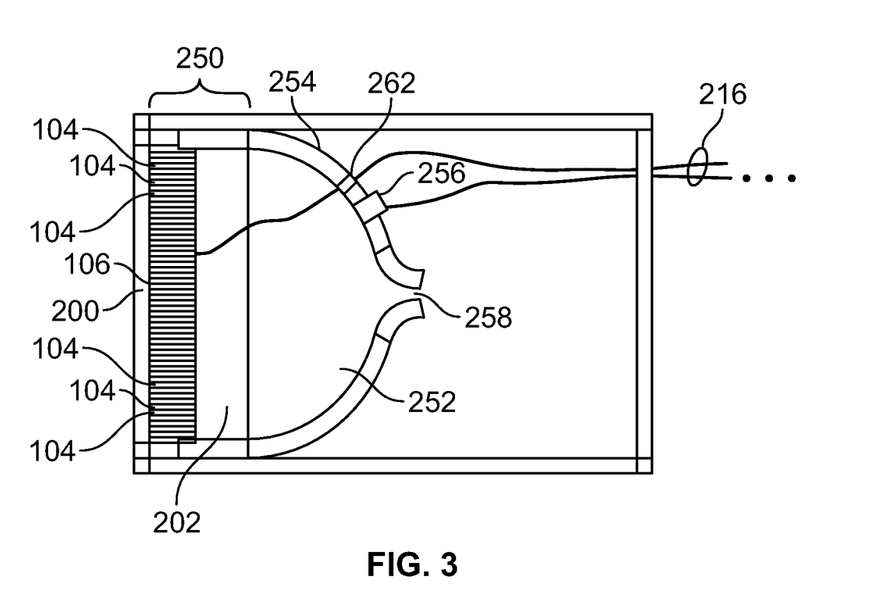
FIG. 3 is an axial cross-sectional view of another embodiment of an acquisition component.

An axial cross-sectional view of another embodiment of an acquisition component is shown in FIG. 3. In this embodiment, multi-element ultrasound transducer 106 comprises a transducer stack 250 (for example, transducer elements 104 and backing 202) and audible sound sensor 204 comprises a Helmholtz resonator 252 with neck 258 behind transducer stack 250. Helmholtz resonator 252 is an air-filled resonator configured by its shape and enclosure material 254 to amplify audible sound. A small air microphone 256 such as an electret microphone is configured to detect the amplified, audible sound. For example, electret microphone 204 is provided on or through enclosure material 254 of Helmholtz resonator 252. Microphone 204 is positioned with its sensing element facing into resonator 252, or is otherwise configured to detect the amplified, audible sound. Helmholtz resonator 252 may also have a small, sealed entrance and/or egress point 262 for an electrical cable for transducer stack 250, or neck 258 may be used for this purpose. A combination cable 216 from transducer stack 250 and microphone 204 can be arranged similarly to the arrangements described with respect to the embodiments of FIG. 1 described herein, and an earphone or headphone may likewise be provided.

The above-described acquisition component embodiments advantageously sense sound and ultrasound through the same surface, footprint, or sensing area simultaneously (e.g., the portion of the lens in contact with an object such as a patient's body), with only one part of the acquisition component touching the patient or other object.

Figure 4:
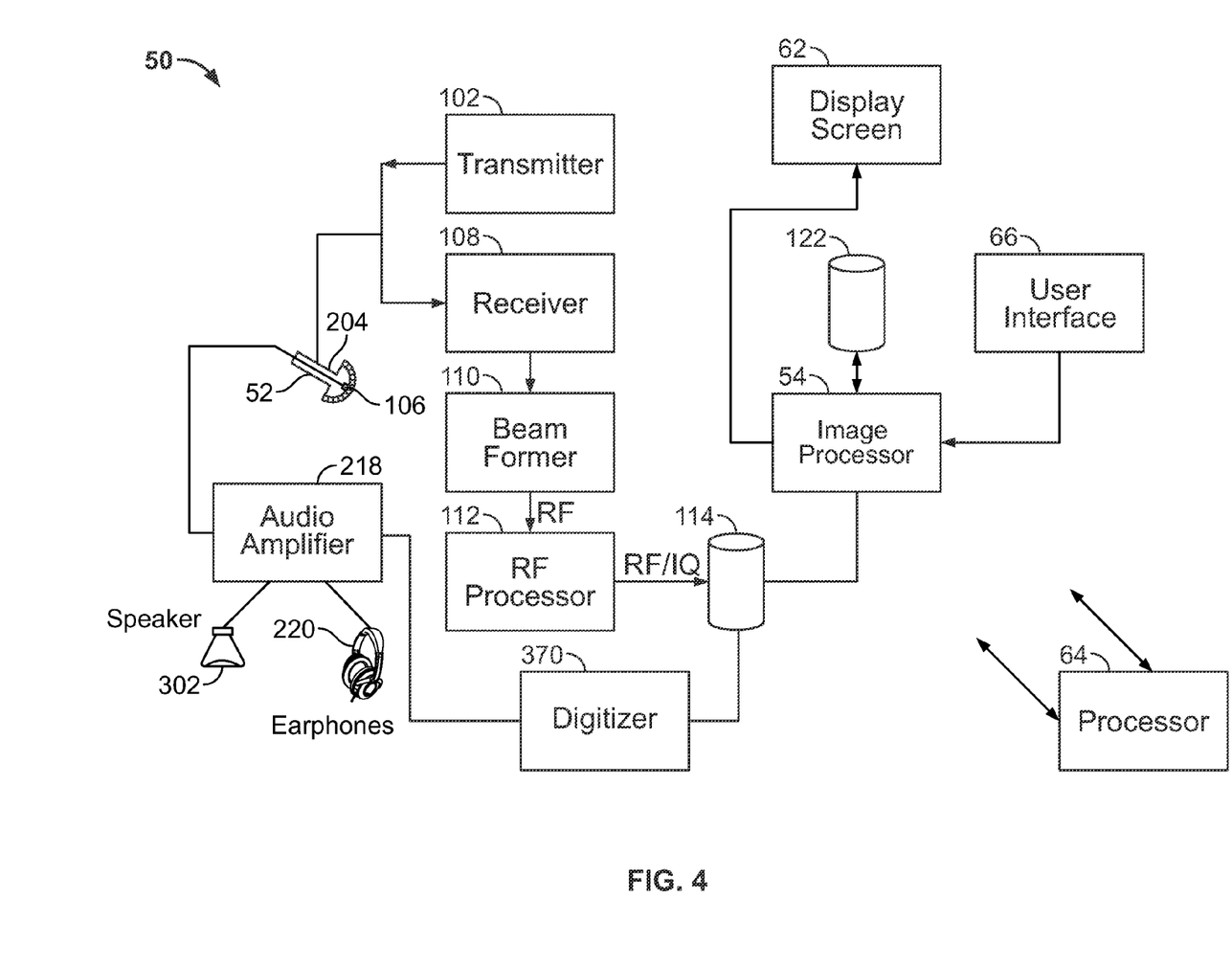
FIG. 4 is a block diagram of an inspection apparatus constructed in accordance with an embodiment of the invention.

In some embodiments of the present invention, an inspection apparatus 50 is provided, as shown in the block diagram of FIG. 4. Inspection apparatus 50 is under control of processor 64 and includes a transmitter 102 that drives an array of elements (e.g., piezoelectric elements) within a multi-element ultrasound transducer 106 to emit pulsed ultrasonic signals into an object, for example, a patient's body. The ultrasonic signals are back-scattered from structures in the body, like blood cells or muscular tissue, to produce echoes that return to multi-element ultrasound transducer 106. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

The inspection apparatus 50 also includes an image processor 54 to process the acquired ultrasound information (e.g., RF signal data or IQ data pairs) and prepare frames of ultrasound information for display 62. The image processor 54 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 during a scanning session and the processed and displayed in off-line operation.

The image processor 54 is connected to a user interface 64 that may control operation of the image processor 54. The display 62 includes one or more monitors that present patient information, including diagnostic ultrasound images to the user for diagnosis and analysis. One or both of memory 114 and memory 122 may store three-dimensional data sets of the ultrasound data, where such 3-D data sets are accessed to present 2-D and 3-D images. The images may be modified and the display settings of the display 118 also manually adjusted using the user interface 66.

The inspection apparatus 50 may obtain volumetric data sets by various techniques (e.g., 3D scanning, real-time 3D imaging, volume scanning, 2D scanning with transducers having positioning sensors, freehand scanning using a Voxel correlation technique, 2D or matrix array transducers and the like). The multi-element ultrasound transducer 106 is moved, such as along a linear or arcuate path, while scanning a region of interest (ROI). At each linear or arcuate position, the transducer 106 obtains scan planes that are stored in the memory 114.

In the meantime, while multi-element ultrasound transducer 106 is operating, audible sound sensor 204 is also operating by providing an audio signal to audio amplifier 218. Audio amplifier 218 drives speaker 302 and/or headphones or earphones 220. Also, in the illustrated embodiment, a digitizer 370 is provided that allows the audible sound sensed by audible sound sensor 204 to be recorded in memory 114 and/or memory 122.

Figure 5:
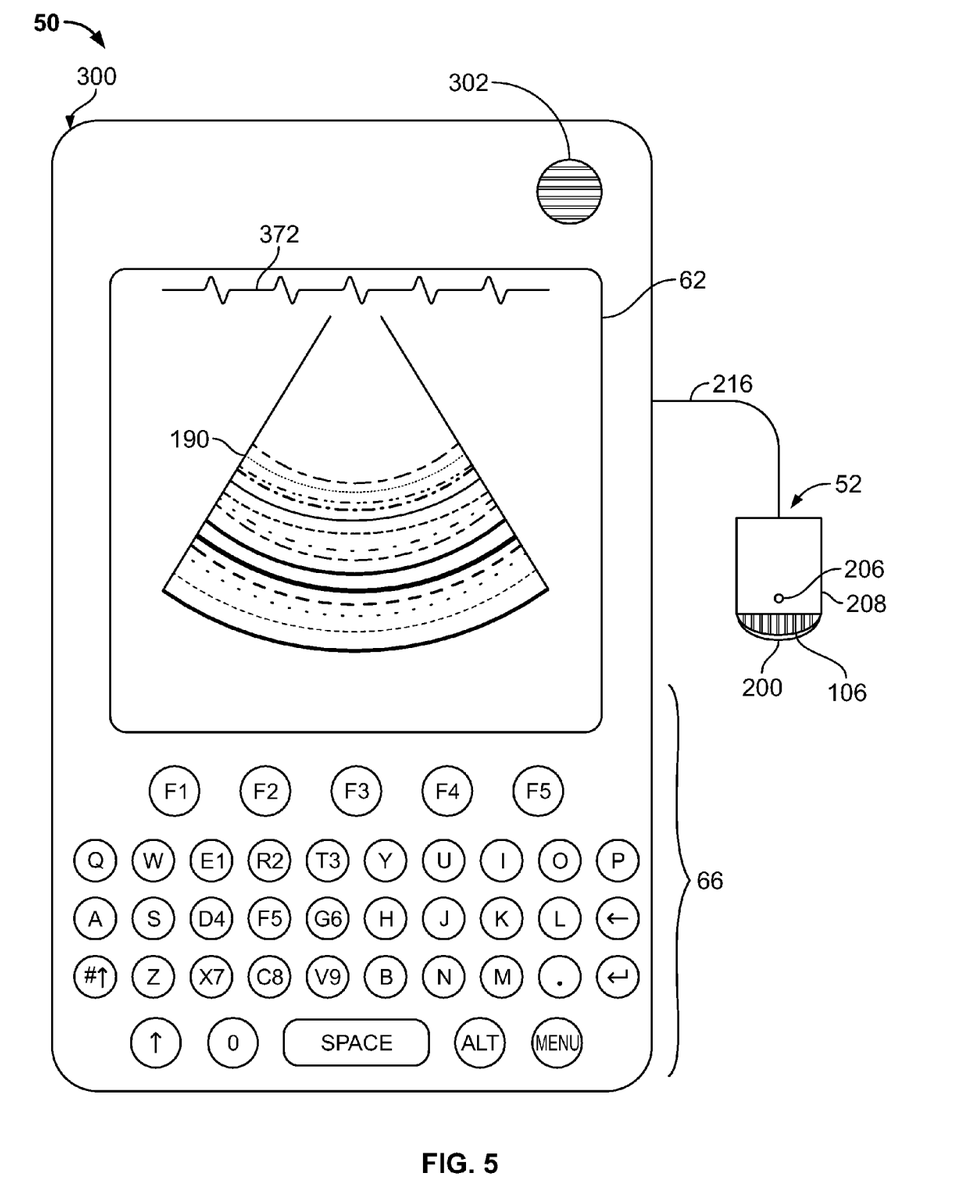
FIG. 5 is a pictorial diagram of a pocket-sized inspection apparatus embodiment that includes an acquisition component that contains an audible sound sensor configured to receive audible sounds within a sensing area and a multi-element ultrasound transducer configured to emit ultrasound signals and to receive reflections of the ultrasound signals within the same sensing area.

FIG. 5 is a pictorial diagram of a pocket-sized inspection apparatus 50 that includes an acquisition component 52 that contains an audible sound sensor 204 (not visible in FIG. 5) configured to receive audible sounds within a sensing area and a multi-element ultrasound transducer 106 configured to emit ultrasound signals and to receive reflections of the ultrasound signals in the same sensing area. The sensing area is essentially the area of a patient or object covered by lens 200. Audible sound sensor 204 and multi-element ultrasound transducer 106 are configured to be simultaneously operable or separately operable. Also provided in these embodiments is a hand-held (or portable) console 300 that includes within (see FIG. 4) an ultrasound transmitter 102, an ultrasound receiver 108, a processor 64 and a display screen 62. The hand-held or portable console 300 is configured to display an image 190 in accordance with the received, reflected ultrasound signals. Also included in inspection apparatus 50 is an audible sound receiver (e.g., an audio amplifier 218), so that inspection apparatus 50 is configured to produce audible sounds in accordance with the received audible sounds. Audio amplifier 218 is not shown in FIG. 5, but is shown in FIG. 4. In some embodiments of inspection apparatus 50, audio amplifier 218 is inside housing 208 of acquisition component 52 or inside a housing of hand-held or portable console 300. However, an audio amplifier 218 separate from acquisition component 52 and console 300 can be used in some embodiments of the present invention. In some configurations, audio amplifier 218 is provided with an earphone or a headphone 220 (shown in FIG. 4) and/or a speaker 302. Speaker 302 may be mounted inside console 300, as shown in FIG. 5.

As described above in conjunction with other embodiments, and referring to FIG. 5 as well as FIGS. 1-4, the multi-element ultrasound transducer 106 can comprise a backing 202, and the audible sound sensor 204 can be mounted on or behind the backing of the multi-element ultrasound transducer. Also, acquisition component 52 may further include at least one switch 206 configured to selectively enable or disable audible sound sensor 204 and/or multi-element ultrasound transducer 106. Furthermore, in some embodiments, the multi-element ultrasound transducer 106 further comprises a transducer stack 250 and the audible sound sensor 204 further comprises a Helmholtz resonator 252 behind the transducer stack that is configured to amplify audible sound. An air microphone 256 may be used to detect the amplified, audible sound. Also, a speaker may be provided to reproduce the audible sounds received by the audible sound sensor 204.

In some embodiments of inspection apparatus 50, console 300 is further configured (e.g., by software in memory) to display an audio spectrum or a phonocardiogram 372 derived from the received audible sound, and/or record a representation of the received audible sounds on either an analog or digital recording medium, such as memory 114. This embodiment has an added clinical advantage in that is particularly easy to co-register heart sounds and an echocardiogram.

Figure 6:
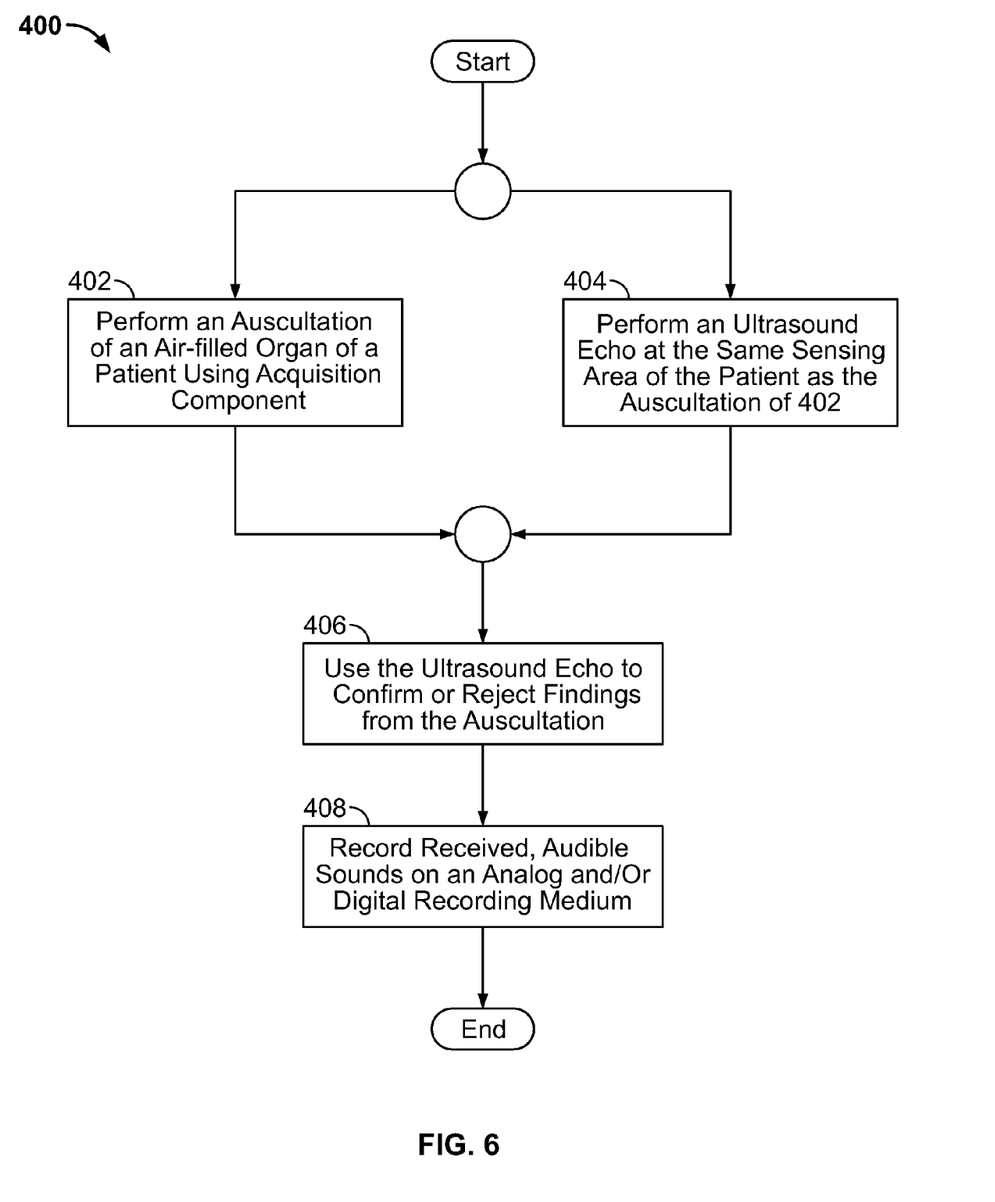
FIG. 6 is a flow chart of a method for performing auscultation using an embodiment of an inspection apparatus.

Some embodiments of the present invention provide a method for performing auscultation using an inspection apparatus 50. A flow chart 400 of such a method is shown in FIG. 6. The method includes, at 402, performing an auscultation of an organ of a patient (for example, and not by way of limitation, an air-filled organ) using acquisition component 52 at a sensing area of the patient, while simultaneously, at 404, performing an ultrasound echo at the same sensing area of the patient. The method next includes, at 406, using the ultrasound echo to confirm or reject findings from the auscultation, or to add new knowledge by the combination. For the use of an ultrasound echo to confirm or reject findings from the auscultation, see, for example, T. Xie et al., "Rapid screening of cardiac patients with a miniaturized hand-held ultrasound imager—comparisons with physical examination and conventional two-dimensional echocardiography," Clin Cardiol. 2004 Apr.;27/4:241-5, W. L. Duvall et al., "Can hand-carried ultrasound devices be extended for use by the noncardiology medical community?" Echocardiography. 2003Jul.;20/5:471-6, M. N. Kotler et al., "Echocardiographic and phonocardiographic correlation of heart sounds and murmurs," Cardiovasc Clin. 1978;9/2:39-57, and R. Salerni et al., "Noninvasive graphic evaluation: phonocardiography and echocardiography," Cardiovasc Clin. 1986; 16/2:173-210.

An earphone operably coupled to the audible sound sensor can be used to perform the auscultation, or a speaker housed within the console can be used to perform the auscultation. In some embodiments, at 408, the received audible sounds are recorded on an analog and/or digital recording medium.

By way of example, the pocket-sized inspection apparatus 50 (exclusive of acquisition apparatus 52 and cable 216) may be a pocket-sized or hand-sized ultrasound system approximately 2 inches wide, approximately 4 inches in length, and approximately 0.5 inches in depth and weigh less than 3 ounces. The display 62 may be, for example, a 320×320 pixel color LCD display (on which a medical image 190 may be displayed). A typewriter-like keyboard may be included in the user interface 66. These dimensions and specifications are to be considered representative of some embodiments rather than limiting.

The various embodiments may also be implemented in connection with full-sized inspection apparatus having different dimensions, weights, and power consumption.

Technical effects of at least one embodiment of the present invention therefore include the integration of sound and ultrasound sensors into a single unit, making it unnecessary for a physician to carry a separate stethoscope, for example, while making rounds. In addition, some embodiments of the present invention are able to perform auscultation and echo simultaneously, without requiring a physician to be exceptionally experienced or having to obtain the services of an assistant. Some embodiments of the present invention have the capability of recording ultrasound images and of enabling a physician to listen to sounds from the body, all from a single sensing area, either separately or simultaneously.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage such as a flash memory stick, secure digital (SD) card and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. An acquisition component comprising:
  an audible sound sensor configured to receive audible sounds within a sensing area;
  a multi-element ultrasound transducer configured to emit ultrasound signals and to receive reflections of said ultrasound signals in said sensing area, wherein said audible sound sensor is disposed behind said multi-element ultrasound transducer within a same housing, and said audible sound sensor and said multi-element ultrasound transducer, are individually controllable to separately operate said audible sound sensor and said multi-element ultrasound transducer to enable or disable operation thereof;
  said multi-element ultrasound transducer connected to a transmitter which drives said multi-element transducer,
  a switch, wherein said audible sound sensor is controllable by said switch to enable or disable operation thereof; and
  a display for displaying an output from at least one of the audible sound sensor or the multi-element ultrasound transducer.

2. The acquisition component of claim 1, wherein said audible sound sensor and said multi-element ultrasound transducer are configured to be simultaneously operable.

3. The acquisition component of claim 1 wherein said audible sound sensor is mounted on or behind a stack of said multi-element ultrasound transducer.

4. The acquisition component of claim 3 wherein said audible sound sensor comprises a member of the group consisting of a mechanically coupled sensor, an accelerometer, a hydrophone, a geophone, and combinations thereof.

5. The acquisition component of claim 1 further comprising an earphone operably coupled to said audible sound sensor.

6. The acquisition component of claim 1 wherein said multi-element ultrasound transducer further comprises a transducer stack and said audible sound sensor further comprises a Helmholtz resonator behind the transducer stack configured to amplify audible sound and an air-coupled microphone configured to detect the amplified, audible sound.

7. The acquisition component of claim 1, wherein said audible sound sensor and said multi-element ultrasound transducer are configured to receive a signal having an ultrasound component and an audible component defining the ultrasound signals and the audible sounds, respectively.

8. The acquisition component of claim 1, wherein the audible sound sensor is configured to receive audible sounds from the received reflections.

9. The acquisition component of claim 1, wherein said audible sound sensor and said multi-element ultrasound transducer are individually controllable to one of turn on said audible sensor and turn off said multi-element ultrasound transducer, turn on said multi-element ultrasound transducer and turn off said audible sensor, turn on both of said audible sensor and said multi-element ultrasound transducer, or turn off both of said audible sensor and said multi-element ultrasound transducer.

10. An inspection apparatus comprising:
  an acquisition component having an audible sound sensor configured to receive audible sounds within a sensing area and a multi-element ultrasound transducer configured to emit ultrasound signals and to receive reflections of said ultrasound signals in said sensing area, wherein said audible sound sensor is disposed behind said multi-element ultrasound transducer within a same housing, and said audible sound sensor and said multi-element ultrasound transducer are individually controllable to separately operate said audible sound sensor and said multi-element ultrasound transducer in an auscultation mode and an ultrasound image acquisition mode, respectively;
  a switch, wherein said audible sound sensor is controllable by said switch to enable or disable operation thereof;
  an ultrasound transmitter, an ultrasound receiver, a processor and a display, said display configured to display an image in accordance with said received, reflected ultrasound signals received by the multi-element ultrasound transducer; and
  an audible sound receiver configured to output the received audible sounds.

11. The inspection apparatus of claim 10 wherein said audible sound sensor and said multi-element ultrasound transducer are configured to be simultaneously operable.

12. The inspection apparatus of claim 10 wherein said audible sound sensor is mounted on or behind a stack of said multi-element ultrasound transducer.

13. The inspection apparatus of claim 10 wherein said audible sound receiver comprises an earphone operably coupled to said audible sound sensor.

14. The inspection apparatus of claim 10 wherein said multi-element ultrasound transducer further comprises a transducer stack and said audible sound sensor further comprises a Helmholtz resonator behind the transducer stack configured to amplify audible sound and an air microphone configured to detect the amplified, audible sound.

15. The inspection apparatus of claim 10 wherein said audible sound receiver is housed within the ultrasound imaging apparatus.

16. The inspection apparatus of claim 14 wherein said audible sound receiver further comprises a speaker.

17. The inspection apparatus of claim 10 wherein said ultrasound imaging apparatus is further configured to display at least one of a phonocardiogram derived from said received audible sound or an audio spectrum derived from said received audible sound.

18. The inspection apparatus of claim 10 wherein said audible sound receiver is further configured to record said received audible sounds on at least one of an analog or digital recording medium.

19. A method for performing auscultation using an inspection apparatus, said method comprising:
  providing an acquisition component having an audible sound sensor configured to receive audible sounds within a sensing area and a multi-element ultrasound transducer configured to emit ultrasound signals and to receive reflections of said ultrasound signals in said sensing area, wherein said audible sound sensor is disposed behind said multi-element ultrasound transducer within a same housing;

providing an ultrasound transmitter, an ultrasound receiver, a processor and a display, said display configured to display an image in accordance with said received, reflected ultrasound signals received by the multi-element ultrasound transducer; and providing an audible sound receiver configured to output the received audible sounds, performing an auscultation of an air-filled organ of a patient using the acquisition component at a sensing area of the patient;

receiving, simultaneously with or separately from said auscultation, an ultrasound echo from the same sensing area of the patient, wherein said audible sound sensor and said multi-element ultrasound transducer are individually controllable to separately operate said audible sound sensor and said multi-element ultrasound transducer to enable or disable operation thereof, said audible sound sensor controllable by a switch to enable or disable operation thereof; and displaying an output from at least one of the audible sound sensor or the multi-element ultrasound transducer.

20. The method of claim 19 further comprising utilizing an earphone operably coupled to the audible sound sensor to perform said auscultation.

21. The method of claim 19 further comprising utilizing a speaker housed within the ultrasound imaging apparatus to perform said auscultation.

* * * * *